(12) United States Patent
Weiher et al.

(10) Patent No.: US 7,048,885 B2
(45) Date of Patent: May 23, 2006

(54) METHOD AND APPARATUS FOR FORMING AN EMBOSSED ARTICLE

(75) Inventors: Marcus David Weiher, Sherwood, WI (US); Shelley Rae Rasmussen, Oshkosh, WI (US); Andrew Michael Lake, Kimberly, WI (US); Michael John Bott, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 321 days.

(21) Appl. No.: 10/641,802

(22) Filed: Aug. 14, 2003

(65) Prior Publication Data

US 2005/0035492 A1    Feb. 17, 2005

(51) Int. Cl.
*B29C 59/04* (2006.01)
(52) U.S. Cl. ..................................... 264/284
(58) Field of Classification Search ............... 264/284
See application file for complete search history.

(56) References Cited

U.S. PATENT DOCUMENTS

| | | |
|---|---|---|
| 1,357,141 A | 10/1920 | Bibb |
| 2,788,003 A | 4/1957 | Morin |
| 3,494,362 A | 2/1970 | Burgeni |
| 3,874,836 A | 4/1975 | Johnson et al. |
| 3,881,490 A | 5/1975 | Whitehead et al. |
| 4,159,677 A | 7/1979 | Smith |
| 4,289,725 A * | 9/1981 | Muller et al. ............... 264/287 |
| 4,844,965 A | 7/1989 | Foxman |
| 5,173,313 A | 12/1992 | Sato et al. |
| 5,429,630 A | 7/1995 | Beal et al. |
| 5,858,515 A | 1/1999 | Stokes et al. |
| 5,891,118 A | 4/1999 | Toyoshima et al. |
| 5,925,026 A | 7/1999 | Arteman et al. |
| 6,170,393 B1 | 1/2001 | Hook et al. |
| 6,251,207 B1 | 6/2001 | Schultz et al. |
| 6,380,455 B1 | 4/2002 | Moder et al. |
| 2001/0007065 A1 | 7/2001 | Blanchard et al. |
| 2002/0017354 A1 | 2/2002 | Riddell |
| 2002/0197346 A1 | 12/2002 | Papadopoulos |
| 2004/0176734 A1 * | 9/2004 | Rasmussen et al. ........ 604/380 |
| 2005/0064058 A1 * | 3/2005 | Lake et al. ................. 425/194 |

FOREIGN PATENT DOCUMENTS

| | | |
|---|---|---|
| EP | 1 321 286 A1 | 6/2003 |
| GB | 2 370 780 A | 7/2002 |
| WO | WO 90/05514 A1 | 5/1990 |

(Continued)

*Primary Examiner*—Leo B. Tentoni
(74) *Attorney, Agent, or Firm*—Paul Y. Yee

(57) ABSTRACT

An apparatus and process (20) for forming an embossed web or other article can include moving a target, composite web (26) along an appointed machine-direction (22) at a selected web speed, and operatively contacting the target web (26) with a rotary embossing device (38) to thereby form a non-linear embossment region (82) in at least a selected embossment portion of the target web (26). For example, the web speed can be at least a minimum of about 1.9 m/sec. In a particular aspect, the embossing device (38) can include an outer peripheral surface (42) having a lateral cross-direction (24) and a circumferential-direction (40), and can include a non-linear embossing member (44) located on the outer surface (42). In another aspect, the embossing member (44) can be configured to include a selected traversing occurrence along the circumferential-direction (40) of the embossing device (38). In a further aspect, the embossing member (44) can be configured to include a selected lateral traversing distance (50).

25 Claims, 10 Drawing Sheets

FOREIGN PATENT DOCUMENTS

| WO | WO 95/07674 A | 3/1995 |
| WO | WO 97/20107 A1 | 6/1997 |
| WO | WO 97/48551 A1 | 12/1997 |
| WO | WO 98/51250 A | 11/1998 |

* cited by examiner

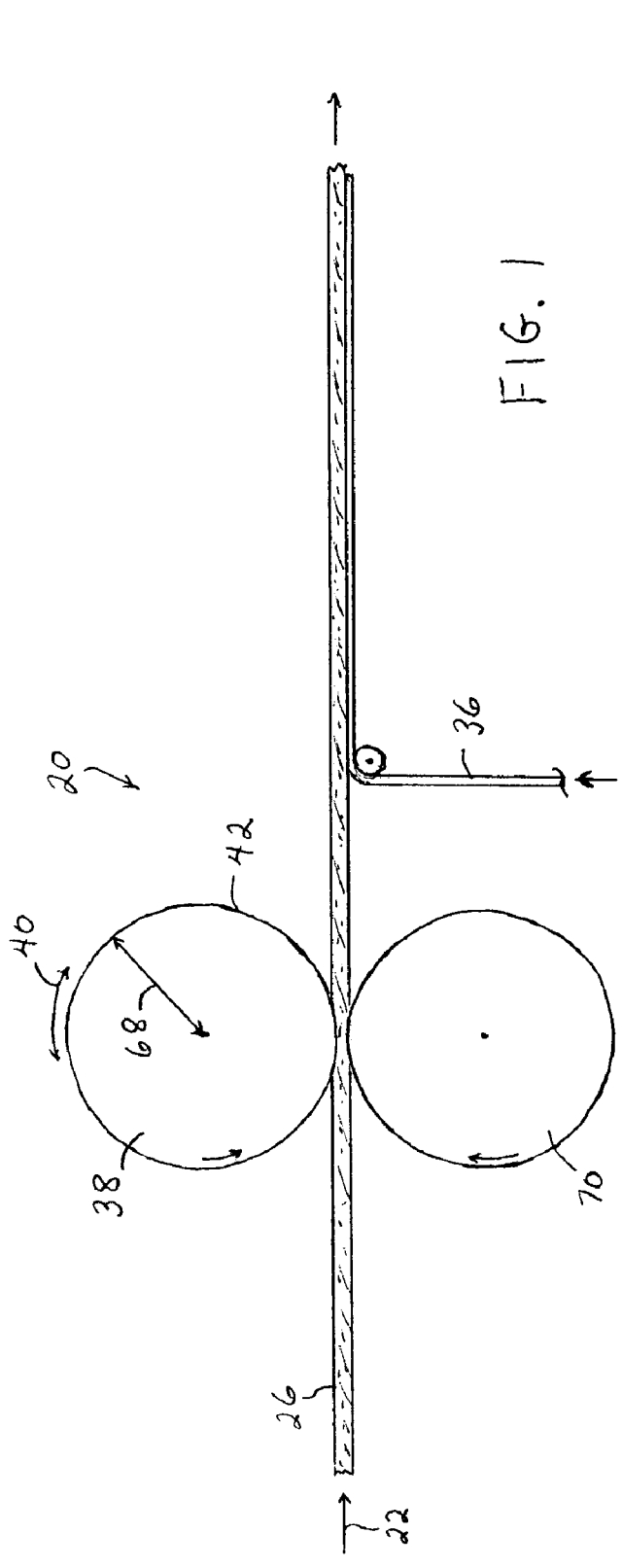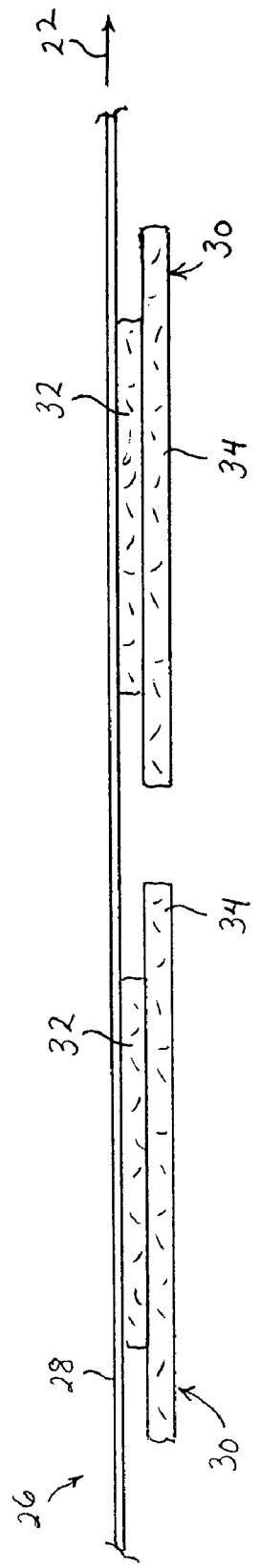

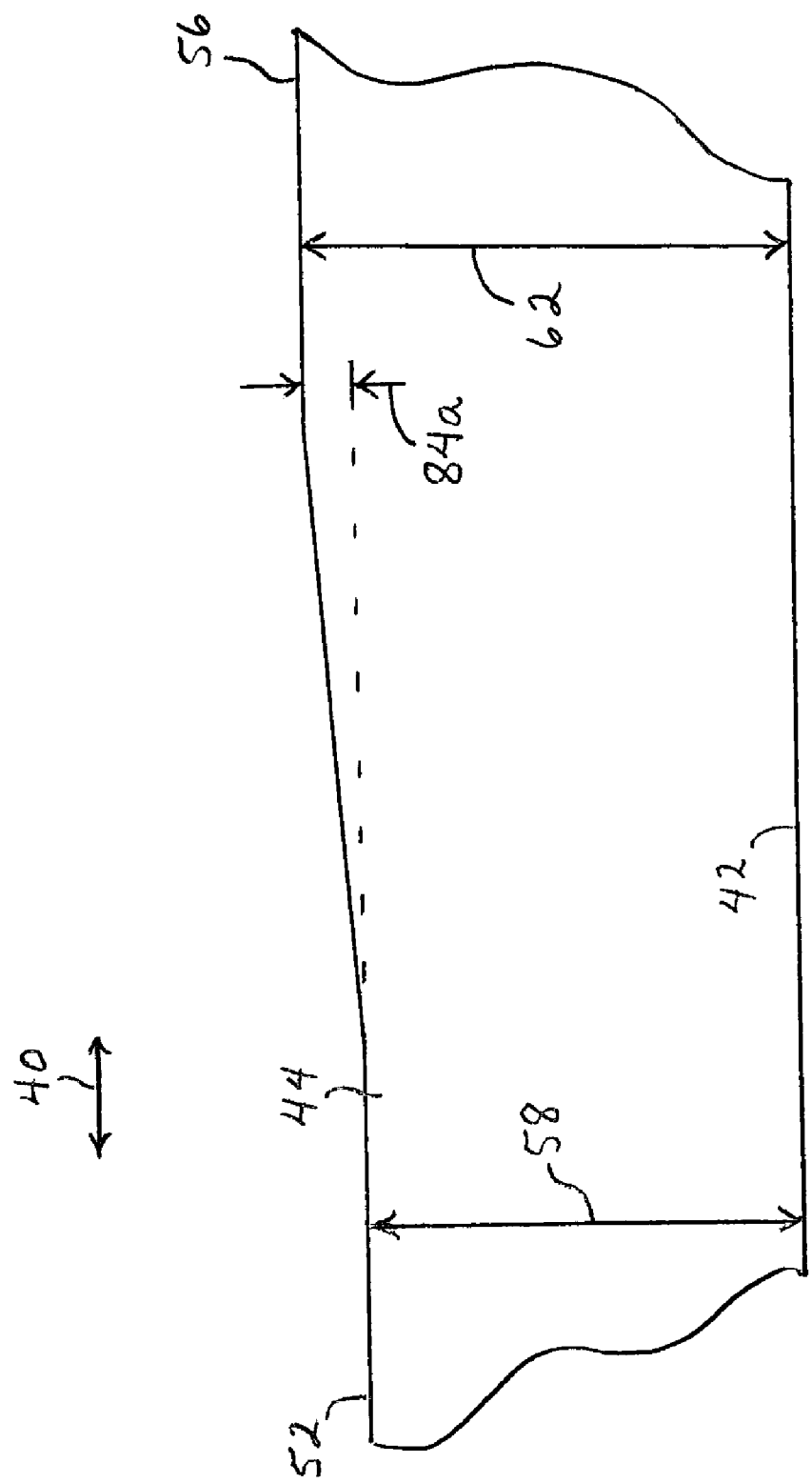

METHOD AND APPARATUS FOR FORMING AN EMBOSSED ARTICLE

FIELD OF THE INVENTION

The present invention relates to an embossing system. More particularly, the present invention pertains to a rotary system for forming an embossed article.

BACKGROUND OF THE INVENTION

Conventional rotary embossing systems have been employed to emboss article webs, and the embossed webs have been employed to produce personal care absorbent articles. Typical embossing systems have included rotary embossing rolls and cooperating, rotary anvil rolls. The embossing rolls have been configured to provide an array of embossing dies to provide embossing lines arranged with selected shapes. Other conventional embossing systems have also included bonding components for providing construction bonds. In particular systems, the construction bonds have been located proximate the regions of article web where the article web has been embossed. Typically, the operating speed of the embossing system has been limited by the available embossing force and by the amount of dwell time needed to reliably form the desired embossments. With conventional systems, the embossing operation has typically been performed prior to a cutting operation that separates the article web into individual articles.

To maintain the integrity of the article web, the operating speed of conventional embossing systems has been limited. High-speed embossing operations have required high levels of embossing force, and the high embossing force has caused an undesired cutting or breaking of one or more component layers of the article web. In addition, the high speed embossing operation has made it difficult to provide sufficient levels of dwell time during which the embossing can be conducted. The low dwell time has excessively reduced the reliability of the embossing operation. As a result, there has been a continued need for a high speed embossing method and apparatus that can more efficiently and more reliably form desired embossments while substantially avoiding any excessive cutting or breakage of the article web.

BRIEF DESCRIPTION OF THE INVENTION

Generally stated, the present invention can provide an apparatus and process for forming an embossed web or other article. The apparatus and process can include moving a target web along an appointed machine-direction at a selected web speed, and operatively contacting the target web with a rotary embossing device to thereby form a non-linear embossment region in at least an appointed embossment portion of the target web. The embossing device can include an outer peripheral surface having a lateral cross-direction and a circumferential-direction, and can include a non-linear embossing member located on the outer surface. In a particular feature, the embossing member can be configured to include a traversing occurrence of at least about 1 back-and-forth cycle within a 5 cm length along the circumferential-direction of the embossing device. In another feature, the embossing member can be configured to include a lateral traversing distance which is at least about 0.5 cm and not more than about 0.8 cm.

By incorporating its various aspects and configurations, the apparatus and method of the present invention can more reliably and more effectively emboss the target web. The desired embossing can be more consistently accomplished at high speed while substantially avoiding undesired cuts or breaks of the component portions of the target web. The apparatus and method can also more effectively produce embossed regions that are more uniformly defined, and can provide an embossed target web having improved integrity and a desired controlled deformation.

BRIEF DESCRIPTION OF THE DRAWINGS

The various features, aspects and advantages of the present invention will become better understood with reference to the following description, appended claims and accompanying drawings where:

FIG. 1 shows a schematic, side elevational view of a representative method and apparatus for selectively embossing an appointed target web.

FIG. 1A shows an enlarged, schematic, side view of a representative longitudinal cross-section through a portion of an appointed target web.

FIG. 7A shows an enlarged view of another stepped region of the embossing member illustrated in FIG. 4.

DETAILED DESCRIPTION OF THE INVENTION

Figure 2:
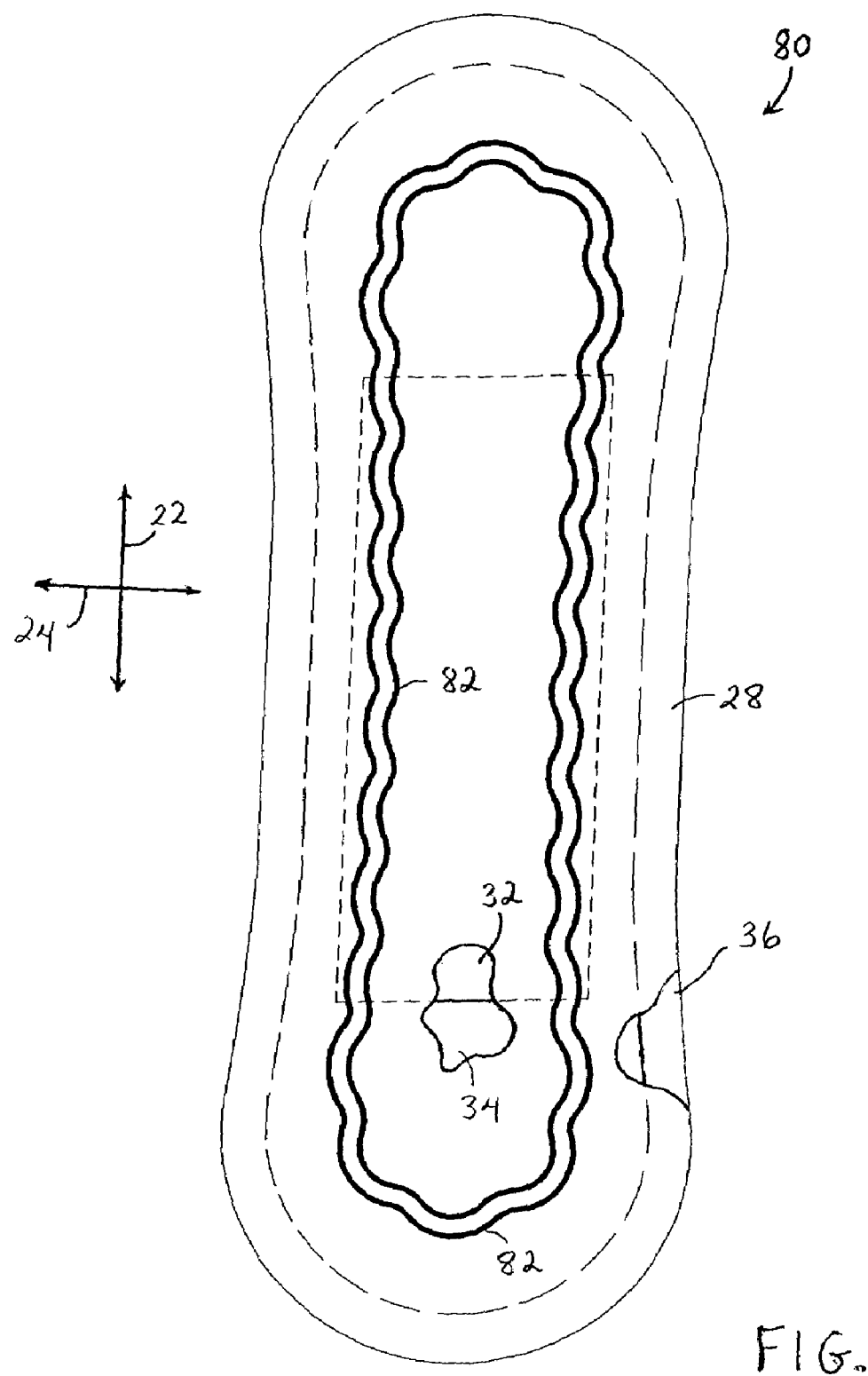
FIG. 2 shows a representative, partially cut-away plan view of a bodyside of a representative web-segment or article that can be produced with the method and apparatus of the invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid distribution layers, barrier layers, and the like, as well as combinations thereof.

Disposable absorbent articles and the components thereof, can operate to provide a body-facing surface and a garment-facing surface. As used herein, "body-facing surface" means that surface of the article or component which is intended to be disposed toward or placed adjacent to the body of the wearer during ordinary use, while the "outward surface" or "outward-facing surface" is on the opposite side, and is intended to be disposed to face away from the wearer's body during ordinary use. The outward surface may be arranged to face toward or placed adjacent to the wearer's undergarments when the absorbent article is worn.

With reference to FIGS. 1 and 2, the method and apparatus of the invention can have an appointed machine-direction 22 which extends longitudinally, and an appointed lateral cross-direction 24 which extends transversely. For the purposes of the present disclosure, the machine-direction 22 is the direction along which a particular component or material is transported length-wise along and through a particular, local position of the apparatus and method. The cross-direction 24 lies generally within the plane of the material being transported through the method and apparatus, and is aligned perpendicular to the local machine-direction 22. Accordingly, in the view of the arrangement representatively shown in FIG. 1, the cross-direction 24 extends perpendicular to the plane of the sheet of the drawing.

Figure 2A:
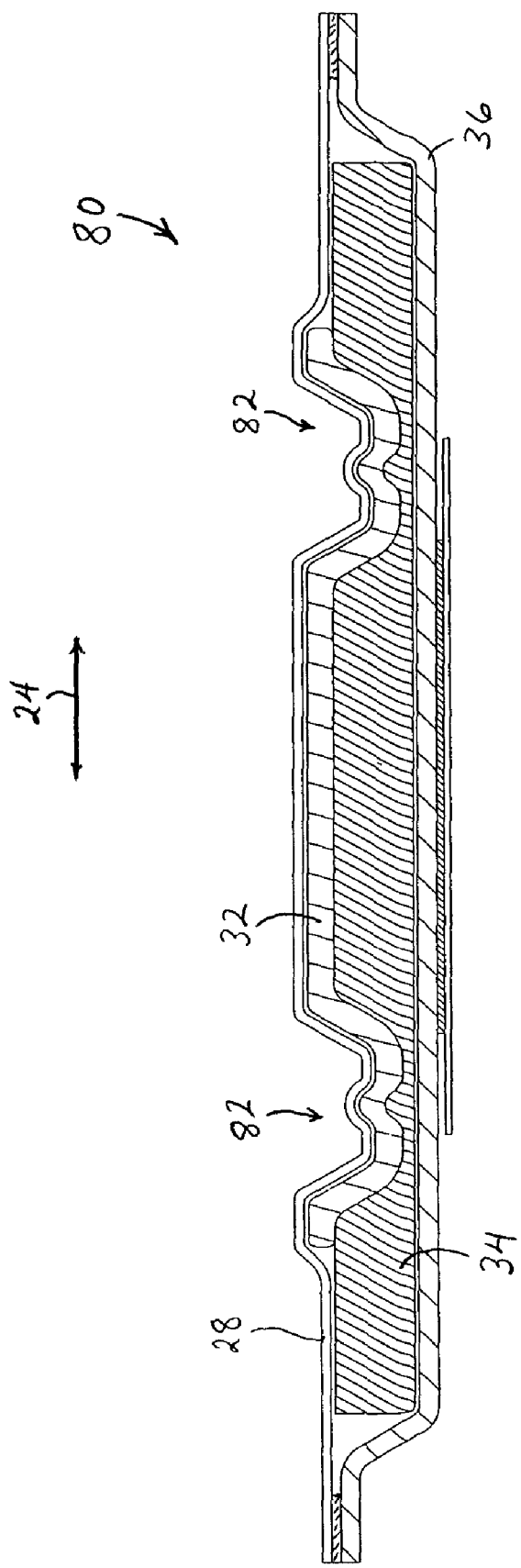
FIG. 2A shows a representative, enlarged view of a transverse cross-section through a representative web-segment or article that can be produced with the method and apparatus of the invention.
Figure 3:
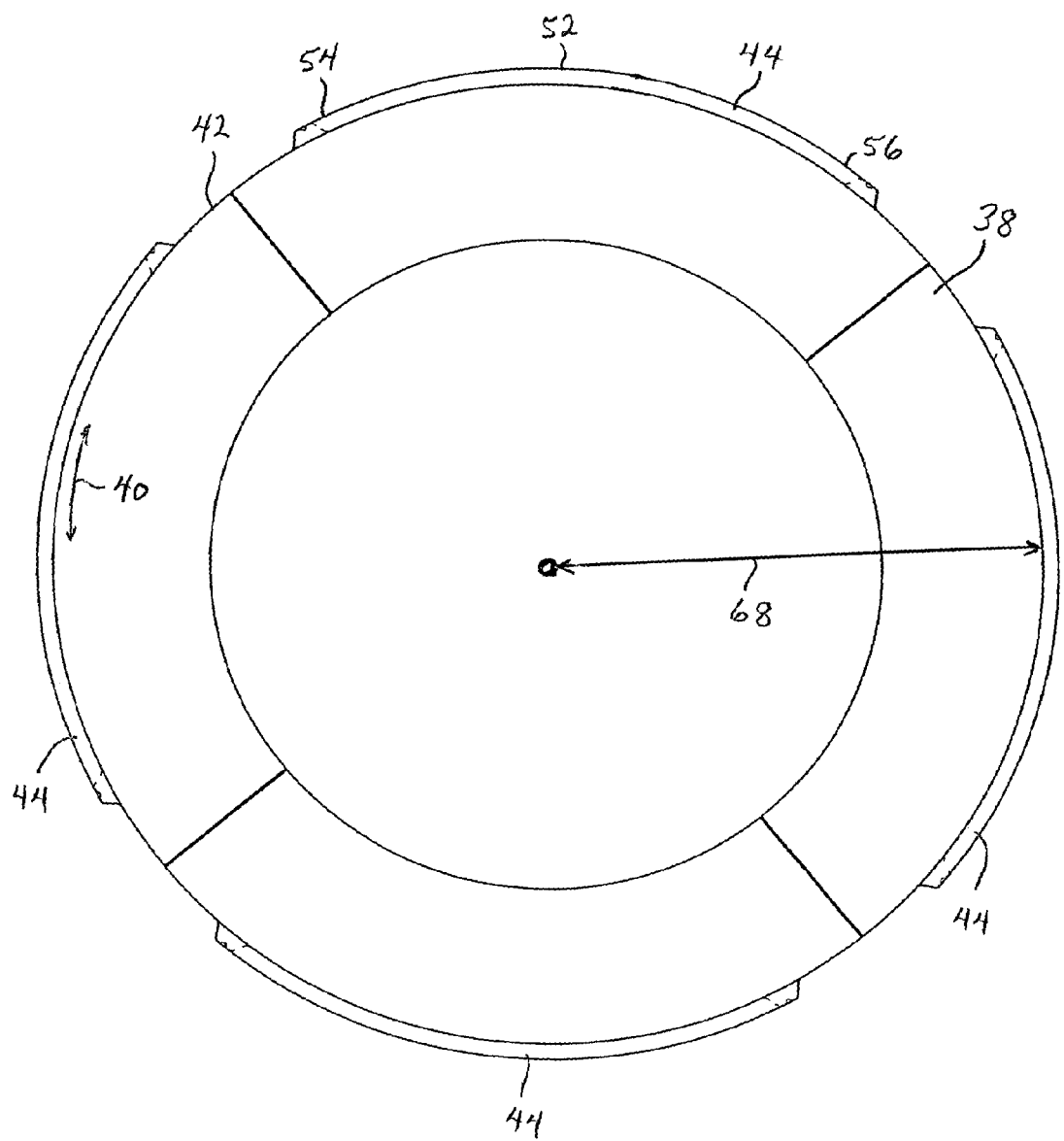
FIG. 3 shows a representative side view of a rotary embossing device that can be employed with the present invention.
Figure 4:
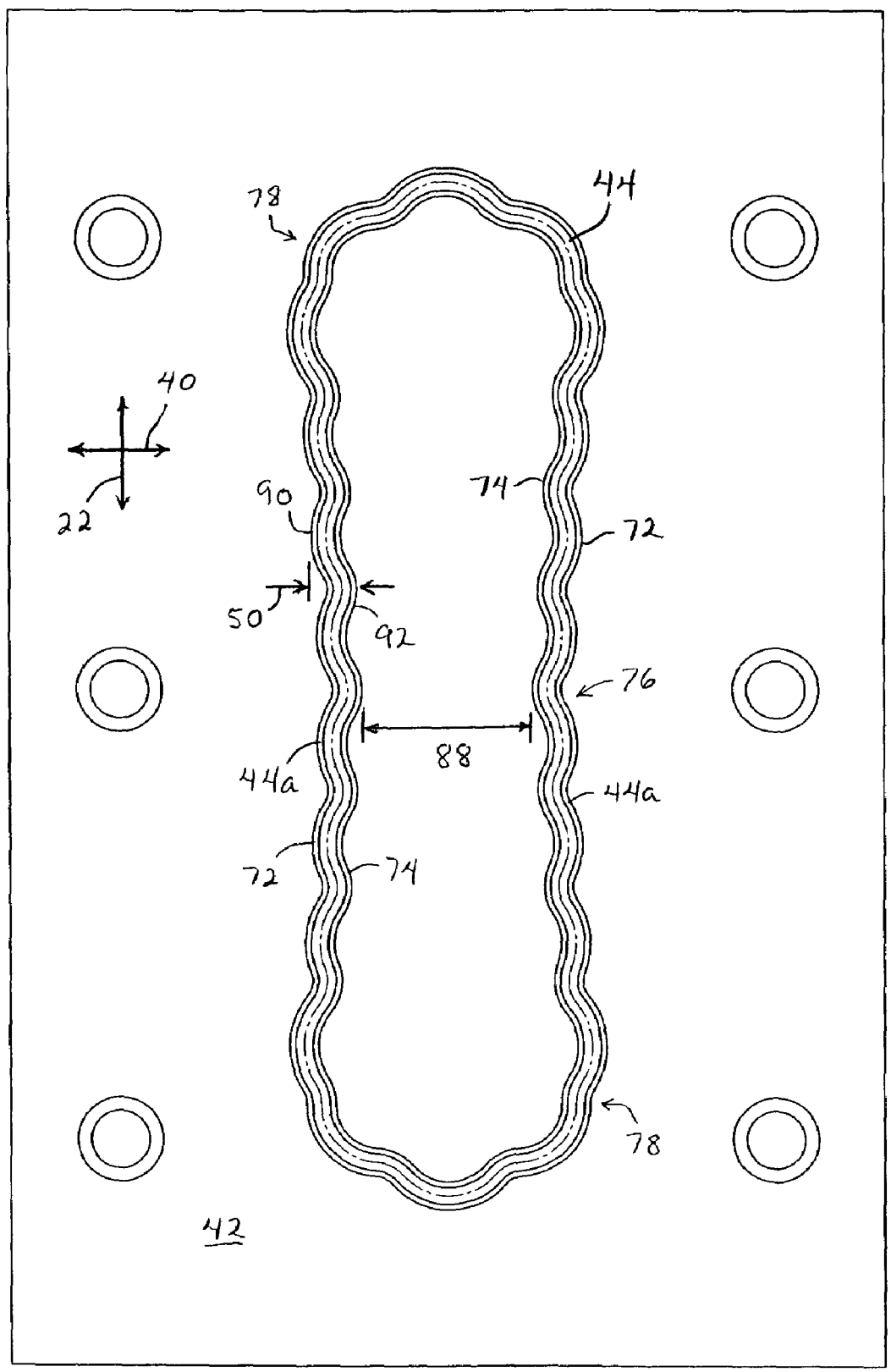
FIG. 4 shows a top view of a representative embossing member where, for the purpose of illustration and clarity, the embossing member has been "flattened" to remove its circumferential curvature.

With reference to FIGS. 1, 3 and 4, the embossing apparatus and process 20 for forming an embossed web or other article can include moving a target web 26 along an appointed machine-direction 22 at a selected web speed, and operatively contacting the target web 26 with a rotary embossing device 38 to thereby form a non-linear embossment region 82 in at least an appointed embossment portion of the target web 26. In a particular, aspect the web speed can be at least a minimum of about 1.9 m/sec. The embossing device 38 can include an outer peripheral surface 42 having a lateral cross-direction 24 and a circumferential-direction 40, and can include a non-linear embossing member 44 located on the outer surface 42. In a particular feature, the embossing member 44 can be configured to include a traversing occurrence of at least about 1 back-and-forth cycle within a 5 cm length along the circumferential-direction 40 of the embossing device 38. In another feature, the embossing member 44 can be configured to include a lateral traversing distance 50 which is at least about 0.1 cm. Additionally, the traversing distance can be up to about 2.3 cm. Another feature of the embossing method and apparatus can include an anvil member 70 which has been configured to cooperate with the rotary embossing device 38. The anvil member can be a rotary anvil. Additionally, the anvil member can be arranged to provide an operative embossing region which can be located in a nip region between the rotary embossing device 38 and the anvil 70. Conventional rotary anvils are well known and are available from commercial vendors. A further feature of the apparatus and process can include an attaching of the target web 26 to a web of baffle material 36. In a particular aspect, the attaching of the baffle web 36 can be conducted after the contacting of the composite web 26 with the rotary embossing device 38. In additional aspects, the target web 26 can be a multi-component, composite web, and the composite web or other target web can be cut or otherwise divided to provide individual web segments or articles 80, such as the feminine care article representatively shown in FIGS. 2 and 2A. The feminine care article can, for example, be a feminine care pad or panty-liner, and the article can have a lengthwise-dimension along the longitudinal direction 22, and a transverse-dimension along the laterally extending, cross-direction 24.

By incorporating its various aspects, features and configuration, alone or in combination, the apparatus and method of the present invention can more efficiently and more effectively emboss a target web. The target web can be embossed with a reduced occurrence of puckering and wrinkling in the embossed regions, and the embossing can be accomplished while substantially avoiding undesired breaks or fractures of component portions of the target web. The apparatus and method can also help eliminate the need for additional processing equipment, and can help reduce manufacturing costs.

In the construction of an operative composite article web 26, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

With reference to FIGS. 1 and 1A, the target web 26 can be configured to move at a selected speed along the machine-direction 22 of the apparatus and method. The target web may be composed of a single material, but desirably can be a composite web which includes a plurality of materials. In the representatively shown configuration, the target web can include an extending substrate web, and at least one absorbent body member 30. In a desired configuration, the composite target web 26 can include a plurality of individual, spaced-apart absorbent body members 30 which are operatively distributed along the machine-directional length of the substrate web. The absorbent body members can also be operatively joined and/or secured to the substrate web. Various known, conventional mechanisms can be employed to position individual absorbent body members 30 at the desired spaced-apart locations along the machine-direction 22 of the method and apparatus. As representatively shown, the substrate web can be a web of cover material 28. Other webs may optionally be employed, as desired.

The topsheet or cover layer web 28 may include a web constructed of any operative material, and may be a composite material. For example, the cover layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

Each absorbent body member 30 can include cellulosic fibers, and the absorbent body member may have a non-uniform structure or may have a substantially uniform structure, as desired. In a particular arrangement, the absorbent body 30 can include one or more component layers. As representatively shown, the absorbent body 30 can include a first absorbent layer portion 32 and at least a second absorbent layer portion 34. The component layer portions may be composed of different materials or may be composed of substantially the same material.

The structure of the absorbent body 30 can be operatively configured to provide desired levels of absorbency and storage capacity, and desired levels of liquid acquisition and distribution. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material. The absorbent fiber can include natural fiber, such as cellulosic fibers, and/or synthetic fiber, such as synthetic polymer fibers. The absorbent body may also include one or more components that can modify menses or inter-menstrual liquids.

The absorbent structure 30 may also include superabsorbent material. Superabsorbent materials suitable for use in the present invention are known to those skilled in the art, and may be in any operative form, such as particulate form.

Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as the Dow Chemical Company and Stockhausen, Inc. The superabsorbent material may desirably be included in an appointed storage or retention portion of the absorbent system, and may optionally be employed in other components or portions of the absorbent article.

The first absorbent layer portion 32 may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the first absorbent layer portion 32 may include a selected quantity of superabsorbent materials, as desired. In a particular aspect, the fibrous material of the first absorbent layer portion can be substantially free of debonding agents. The first absorbent layer portion may also include one or more components that can modify menses or inter-menstrual liquid.

In a particular arrangement, the first absorbent layer portion 32 can be composed of a thermally-bonded stabilized-airlaid fibrous web (e.g. Concert product code DT200.100.D0001), which is available from Concert Industries, a business having offices located in Gatineaux, Quebec, Canada.

The second absorbent layer portion 34 may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the second absorbent layer portion 34 can include a selected quantity of superabsorbent materials. In a particular aspect, the fibrous material of the second absorbent layer portion can be substantially free of debonding agents. In other aspects, the fibrous second absorbent layer portion may include a friction-reducing material, which can help increase the flexibility of the article in its formed embossment regions 82. The second absorbent layer portion 34 may also include one or more components that can modify menses or inter-menstrual liquids In a particular arrangement, the second absorbent layer portion 34 can include a fibrous, non-debonded, southern pine kraft woodpulp (e.g. NB 416), which is available from Weyerhaeuser, a business having offices located in Federal Way, Wash., U.S.A. In another arrangement, the shaping layer can include a fibrous woodpulp treated with an agent that helps enable densification and helps reduce stiffness (e.g. ND 416; which is also available from Weyerhaeuser).

Each absorbent layer portion 32, 34 can have a corresponding machine-directional length, and cross-directional width. As representatively shown, the length and/or width of the first absorbent layer portion 32 can be smaller than the length and/or width of the second absorbent layer portion 34. Alternatively, the length and/or width of the first absorbent layer portion 32, can be relatively larger than the length and/or width of the second absorbent layer portion 34. As a result, the composite web 26 can have a non-uniform basis weight distribution. Additionally, the composite web can include a non-uniform, z-directional thickness dimension.

The various portions or components of each absorbent body 30 can be joined and/or secured together employing any operative technique. A variety of suitable mechanisms or systems known to one of skill in the art may be utilized to achieve any such secured relation. Examples of such securing mechanisms or systems can include, but are not limited to, the application of adhesives in a variety of patterns between the two adjoining surfaces, entangling at least some portions of one absorbent body component with portions of the adjacent surface of another component, or fusing at least portions of the adjacent surface of one component to portions of another component of the absorbent.

In the representatively shown configuration of the method and apparatus, the components of the target web 26 can be attached with conventional construction adhesive. Any operative adhesive may be employed. Suitable adhesives can, for example, include hot melt adhesives, pressure-sensitive adhesives, solvent-based adhesives, pressure-sensitive adhesives, or the like as well as combinations thereof.

In a particular feature, the cellulosic fibers in one or more portions of the composite target web 26 can be treated with a friction-reducing material, and/or can be configured to be substantially free of any separately provided debonding agent. In another feature, the cellulosic fibers in one or more portions of the composite web 26 can be provided with a moisture content which is at least a minimum of 4 wt %. The moisture content can alternatively be at least about 4.8 wt %. In another aspect, the moisture content can be not more than a maximum of about 11 wt %. The moisture content can alternatively be not more than about 7.2 wt % to provide improved performance. If the moisture content of the cellulosic fibers is too low, the ability to form the desired absorbent body can be degraded due to the generation of static electricity in the forming system. During the embossing process, an excessively low moisture content can result in poor hydrogen bonding, and a poor formation and retention of the desired embossments. If the moisture content of the cellulosic fibers is too high, there can be an undesired growth of microbes in the cellulosic fibers.

In another aspect, the composite web or other target web 26 can be subjected to a selected tension to provide a selected web-strain. Accordingly, the composite web can exhibit a selected web elongation along the machine-direction 22 of the process and apparatus. In a particular aspect, the web-strain can be up to a maximum of about 5%, or more. The web-strain can alternatively be up to about 3%, and can optionally be up to about 2% to provide improved performance. In other aspects, the web strain can be a value greater than 0%. The web strain can alternatively be at least a minimum of about 0.1%, and can optionally be at least about 0.2% to provide further benefits. If the web strain is outside the desired values, the process and apparatus can exhibit a poor formation of the desired embossments, a poor control of the web path, or an excessive cutting or severing of one or more of the materials employed to form the composite web 26. The web strain can be determined by employing the following calculation:

$$\% \text{ web strain} = 100*(L_T-L_O)/L_O$$

where: $L_O$=length of a web portion which is untensioned; $L_T$=length of the same web portion which is tensioned.

A further feature of the apparatus and process can include moving the composite web 26 at a distinctively high web speed. The web speed can be at least a minimum of about 1.9 m/sec (meters per second). The web speed can alternatively be at least about 2.5 m/sec (about 492 feet per minute), and can optionally be at least about 3.0 m/sec (about 590 feet/min) to provide improved performance. In another aspect, the web speed can be up to maximum of about 7.5 m/sec (about 1476 feet/min), or more. The web speed can alternatively be up to about 6.5 m/sec (about 1279 feet/min), and can optionally be up to about 6.0 m/sec (about 1181 feet/min) to provide improved benefits. In other arrangements, the web speed can be up to about 3.5–5.5 m/sec (about 688–1082 feet per min) to provide improved efficiency.

If the web speed is too low, manufacturing costs may become excessive. Additionally, when the web speed is too low, the article may be over embossed, and the article can become excessively stiff. If web speed is too high, the embossments may be poorly formed or defined, due to the reduction in dwell time during which the embossing member can effectively operate and due to the increased rate at which the embossing deformations need to be formed.

The cover layer web 28 or other substrate layer can be delivered into the method and apparatus from a suitable supply source, and an operative attaching technique can be employed to operatively secure the cover web 28 to the absorbent body members 30 by bonding or otherwise attaching all or a portion of the adjacent surfaces to one another. A variety of attaching mechanisms or systems known to one of skill in the art may be utilized to achieve any such secured relation. Examples of such mechanisms or systems include, but are not limited to, the application of adhesives in a variety of patterns between the two adjoining surfaces, entangling at least portions of the adjacent surface of the absorbent with portions of the adjacent surface of the cover, or fusing at least some portions of the cover to portions of the adjacent surface of the absorbent. As representatively shown, a conventional construction adhesive can be employed to assemble together the various components of the desired composite web 26. In a particular aspect, a selected pattern of adhesive can be distributed between the cover layer web 28 and the absorbent body members 30.

Any operative adhesive applicator may be employed. Suitable applicators can include adhesive spray devices, adhesive coating devices, adhesive printing devices, or the like, as well as combinations there of. Any operative adhesive may be employed. Suitable adhesives can, for example, include hot melt adhesives, pressure-sensitive adhesives, solvent-based adhesives, pressure-sensitive adhesives, or the like as well as combinations thereof.

As representatively shown, the rotary embossing device 38 can be configured to provide a rotary embossing roll, and the embossing device can be positioned cooperatively adjacent an anvil member 70. The anvil member 70 can include the representatively shown rotary anvil, which is configured to counter-rotate relative to the rotary embossing device 38. Optionally, the process and apparatus may alternatively include a non-rotary anvil member.

The rotary embossing roll can have a selected roll radius 68. In a particular aspect, the roll radius can be at least a minimum of about 7.5 cm. The roll radius can alternatively be at least about 11 cm, and can optionally be at least about 14 cm to provide improved performance. In another aspect, the roll radius can be up to a maximum of about 32 cm, or more. The roll radius can alternatively be at least about 25 cm, and can optionally be at least about 19 cm to provide improved benefits. If the roll radius is outside the desired values, the method and apparatus can exhibit insufficient dwell time during the embossing operation, or the equipment can require excessive amounts of space and the cost may be prohibitive.

Any conventional power mechanism or system can be employed to drive the rotary embossing device 38. Such power mechanisms can include engines, motors, electromagnetic power systems, fluidic power systems or the like as well as combinations thereof. The selected drive system can be configured to provide the embossing device 38 with a selected surface speed at the outer peripheral rim surface 42, and in a desired arrangement, the peripheral surface speed can be configured to substantially equal the web speed of the target web 26 that is appointed for embossment.

The embossing device 38 can have an outer peripheral rim surface 42 which extends along the circumferential direction 40 and along the axial or transverse cross-direction 24 of the embossing device. With reference to FIGS. 1, 3, 4, 5 and 6, at least one curvilinear or otherwise nonlinear embossing member 44 can be located on the outer peripheral surface 42. In an alternative configuration, a plurality of two or more nonlinear embossing members 44 can be distributed over the outer peripheral surface 42 in a desired array. For example, the plurality of embossing members can be arranged in series along the circumferential direction of the embossing device 38, and the serial arrangement may be irregular or substantially regular, as desired.

Each nonlinear embossing member 44 can include an intermediate portion 76 and end portions 78. With reference to FIG. 4, the nonlinear embossing member 44 can longitudinally extend along the peripheral surface 42 of the embossing device 38 over a distance of at least 4–5 cm along the circumferential direction 40 within the intermediate portion 76 of the embossing member 44. The embossing member 44 can desirably extend circumferentially at least about 6 cm, and can more desirably extend circumferentially at least about 10 cm across the intermediate portion of the embossing member. Generally stated, the intermediate portion 76 is the middle 34 percent (%) of an overall, circumferential length of the embossing member 44. In a particular aspect, the embossing member can extend substantially continuously across the selected circumferential distance in the intermediate portion of the embossing member. Additionally, the curvilinear or otherwise nonlinear embossing member 44 can extend at least partially across the first and/or second end portions 78, 78*a* of the embossing member.

As representatively shown, the embossing member 44 can have a pair of transversely spaced-apart, laterally opposed side-portions 44*a* which extend generally along the circumferential-direction 40 at locations that are appointed to be generally adjacent a pair of laterally opposed side edges of an individual absorbent body 30 during the embossing operation. Additionally, the embossing member 44 can include a circumferentially opposed pair of end-portions 44*b*, and at least a part of the end-portions can extend generally laterally along the cross-direction 24 at positions that can become generally adjacent a pair of circumferentially opposed end edges of the absorbent body during the embossing operation. Either or both of the side-portions 44*a* can be configured to include the various features and aspects attributed to the embossing member. Similarly, either or both of the end-portions 44*b* may include desired features and aspects of the embossing member 44.

The side-portions and end-portions of the embossing member 44 can desirably be configured to provide a desired outline shape, and the embossing member can extend along at least the bodyside of the embossing member to provide the desired shape. The embossing member may also extend along the garment-side surface of the absorbent body 30. In particular examples, the path of the embossing member may provide a symmetrical shape, an asymmetrical shape, a regular or irregular rectilinear shape, a regular or irregular curvilinear shape or the like, as well as combinations thereof. The embossing member may be configured to be discontinuous or substantially continuous, as desired. In particular arrangements, the embossing member 44 can be arranged to effectively provide a substantially closed-shape. In other desired configurations, the embossing member 44 can become located proximate to and relatively inboard from a perimeter edge of a corresponding, individual absorbent body 30 during the embossing operation. In a particular aspect, the embossing member 44 can be configured to extend along substantially an entirety of the absorbent body perimeter during the embossing operation.

The curvilinear or nonlinear embossing member 44 can have a distinctive frequency of its traversing occurrence. As representatively shown in FIGS. 2 and 4, each traversing occurrence can include a single back-and-forth cycle of the pattern array selected for the nonlinear embossing member 44. The occurrence of the traversing cycles may be present in an irregular, non-repeating pattern, in a substantially regular, repeating pattern or in a combination thereof, as desired. Additionally, the traversing frequency can occur along at least the intermediate portion 76 of the embossing member. In particular aspects, the traversing occurrence can be at least a minimum of about 1 cycle. The traversing occurrence can alternatively be at least about 1.2 or 1.5 cycles, and can optionally be at least about 2 cycles to provide improved performance. In other aspects, the traversing occurrence can be up to a maximum of about 10 cycles, or more. The traversing occurrence can alternatively be up to about 8 cycles, and can optionally be up to about 6 cycles to provide improved effectiveness. In a further aspect, the desired number of cycles can be distributed or otherwise arranged to occur with a 5 cm, circumferential length section of the embossing member. If the traversing occurrence is outside the desired values or parameters, the target web 26 and resulting articles 80 can exhibit an excessive pivoting or hinging action along the nonlinear embossment region 82 or an excessive collapsing of the channel structure of the embossment region. Traversing frequencies outside of the desired values may also degrade the embossing operation. For example, there may be a poor formation of the embossments or an undesired cutting of the target web.

As representatively shown, the embossing member 44 can have back-and-forth pattern-shape which can extend over a selective lateral traversing distance 50. The back-and-forth shape can, for example, include an undulating pattern, a serpentine pattern, a zig-zag pattern, a generally sinusoidal pattern, a cycloidal pattern, a semi-cycloidal pattern, a wavy pattern or the like, as well as combinations thereof. The lateral traversing distance 50 can be determined by measuring the lateral distance between the most-outboard-edge to the most-inboard-edge of the nonlinear embossing member 44, as observed during a back-and-forth cycle of the selected, nonlinear embossment pattern. The selected nonlinear pattern can extend a distance of at least 4 cm along the circumferential direction 40 within the intermediate portion 76 of the embossing member. As previously discussed, the back-and-forth nonlinear pattern can optionally extend across a selected circumferential distance within the intermediate portion 76 of the embossing member 44.

The embossing member 44 can alternatively be configured to include a lateral traversing distance 50. In a particular aspect, the lateral traversing distance 50 can be at least a minimum of about 0.1 cm. The lateral traversing distance can alternatively be at least about 0.2 cm, and can optionally be at least about 0.3 cm to provide improved performance. In other aspects, the lateral traversing distance can be up to a maximum of about 2.3 cm, or more. The lateral traversing distance can alternatively be up to about 1.5 cm, and can optionally be up to about 1.1 cm to provide improved effectiveness. A desired arrangement can include a traversing distance which is within the range of about 0.7–0.8 cm.

If the traversing distance 50 is outside the desired values, there can be an excessive pivoting or hinging action along the corresponding embossment region formed in the target web 26. Additionally, there can be an excessive collapsing of the channel structure. Embossing members which traverse beyond the desired values may also result in undesirable stiffness in the edges of the individual product articles 80 formed from the target web 26. The desired values of the various parameters for the traversing, nonlinear embossing member 44 can help reduce the occurrence of excessive puckering or wrinkling of the embossed target, particularly along the section of the target web that is embossed by the intermediate portion 76 of the embossing member. Additionally, the formed articles 80 can exhibit inadequate fit due to an insufficient medial spacing distance 88 (e.g. FIG. 4) between the inboard edges of the laterally opposed sections 44a of the embossing member.

With reference to FIGS. 5 through 7A, the embossing member 44 can have an embossing member height 46 and an embossing member width 48. The embossing member height 46 is the amount of extension/protrusion above a corresponding local outer-surface region of the embossing device. In a particular aspect, the embossing member height can be at least a minimum of about 2 mm. The embossing member height 46 can alternatively be at least about 3 mm, and can optionally be at least about 4.5 mm to provide desired benefits. In another aspect, the embossing member height 46 can be up to a maximum of about 13 mm, or more. The embossing member height can alternatively be up to about 8 mm, and can optionally be up to about 5 mm to provide improved performance. If the embossing member height is too low, the ratio of the embossing member height 46 to the z-directional thickness of the target web 26 can become too low. As a result, an undesired compacting or debulking of the target web may occur within the embossing nip. If the embossing member height 46 is too high, then there can be an excessive risk of equipment failure or damage. For example, portions of the embossing member 44 or associated embossing elements can shear off from the embossing device 38.

Figure 6:
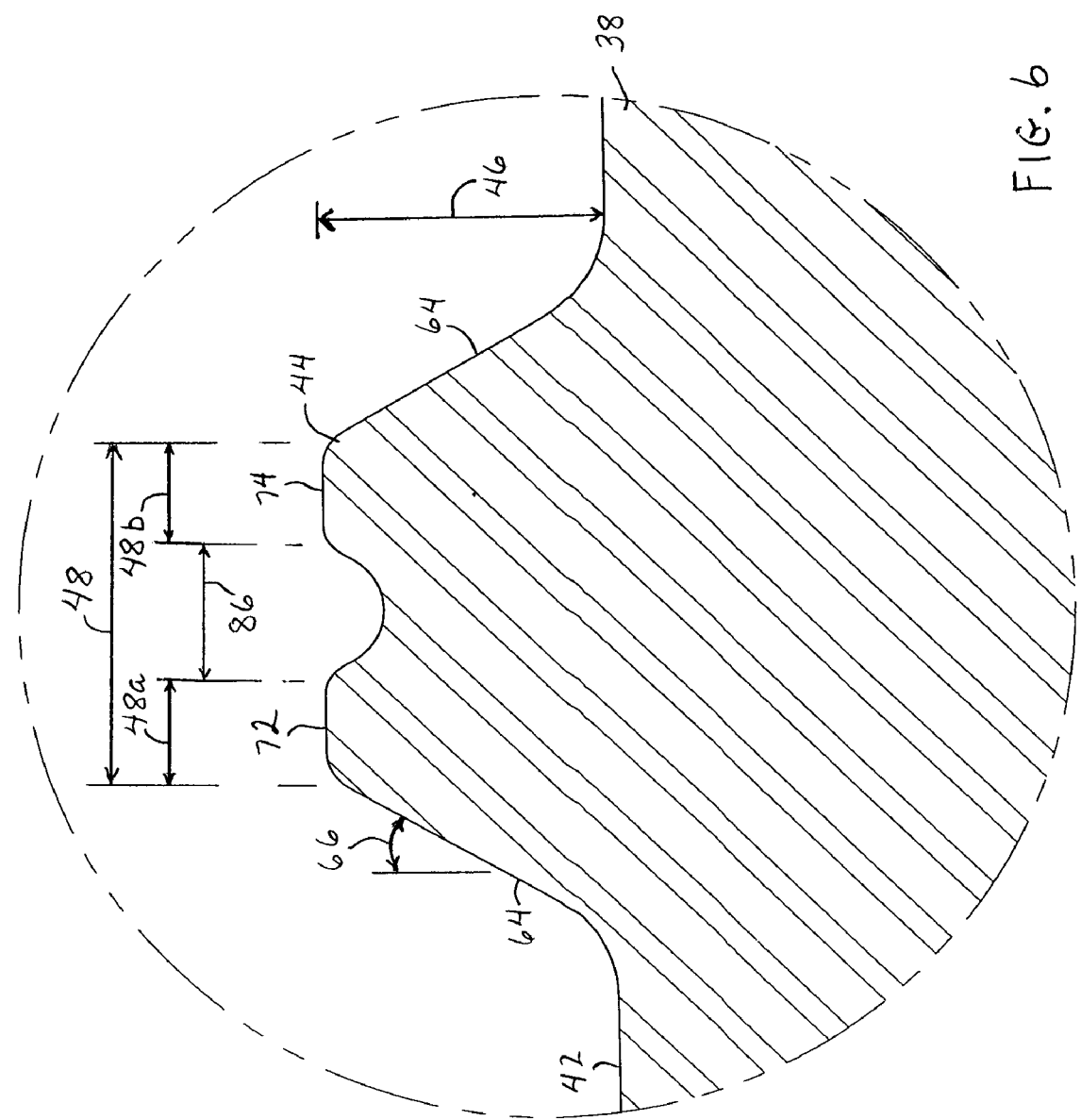
FIG. 6 shows an enlarged view of a cross-section through a representative portion of an embossing member having a plurality of embossing elements.
Figure 6A:
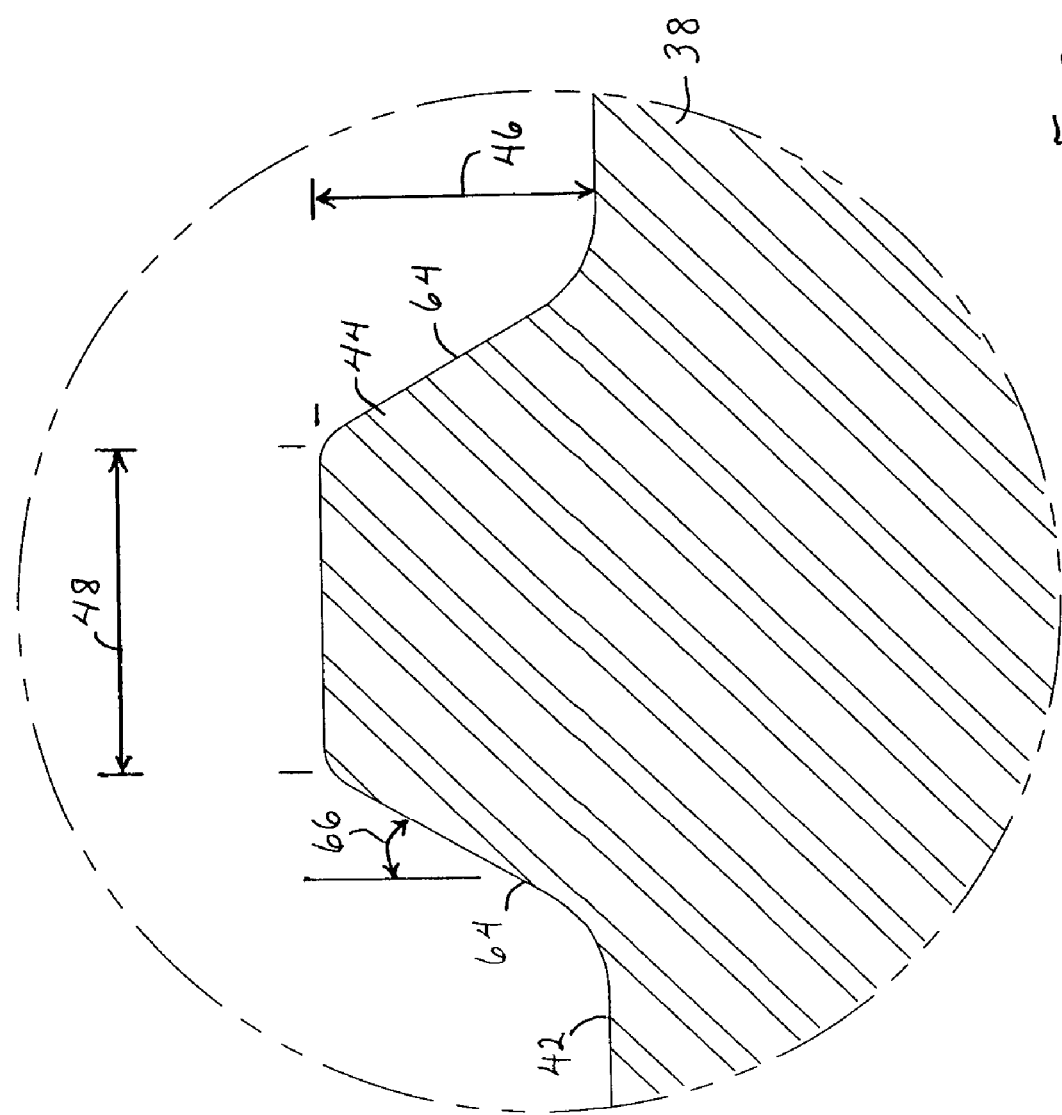
FIG. 6A shows an enlarged view of a cross-section through a representative portion of an alternative embossing member.

With reference to FIG. 6A, the embossing member width 48 can be at least a minimum of about 0.25 mm or 0.5 mm. The embossing member width can alternatively be at least about 0.8 mm, and can optionally be at least about 1 mm to provide improved performance. In another aspect, the embossing member width 48 can be up to a maximum of about 7 mm, or more. The embossing member width can alternatively be up to about 5 mm, and can optionally be up to about 3 mm to provide improved benefits. If the embossing member width 48 is too low there can be an increased risk of undesirably cutting one or more portions or components of the target web 26. If the embossing member width 48 is too wide, the embossed regions can become overly stiff. Additionally, when the embossing member width 48 is too wide, the definition of the embossing pattern can be degraded when the method and apparatus are operating at high speeds and/or with low embossing forces.

The embossing member 44 can include sidewall regions 64, and the sidewall regions can include a distinctive sidewall angle 66. In a particular aspect, the sidewall angle can be at least a minimum of about 5 degrees. The sidewall angle can alternatively be at least about 10 degrees, and can optionally be at least about 20 degrees to provide improved performance. In another feature, the sidewall angle can be up to a maximum of about 45 degrees, or more. The sidewall angle can alternatively be up to about 35 degrees, and can optionally be up to about 30 degrees to provide improved benefits. If the sidewall angle is too small, of if the embossing member is excessively tall or narrow, the embossing member can undesirably break or deform during the operation of the process and apparatus. Additionally, if the sidewall angle is too small, the article may exhibit a bridging of unembossed material across the embossments. If the sidewall angle is too large, the embossing member may undesirably debulk or compact the material of the target web in regions of the target web that are located adjacent to the embossments. As a result, the target web can become excessively stiff.

Figure 5:
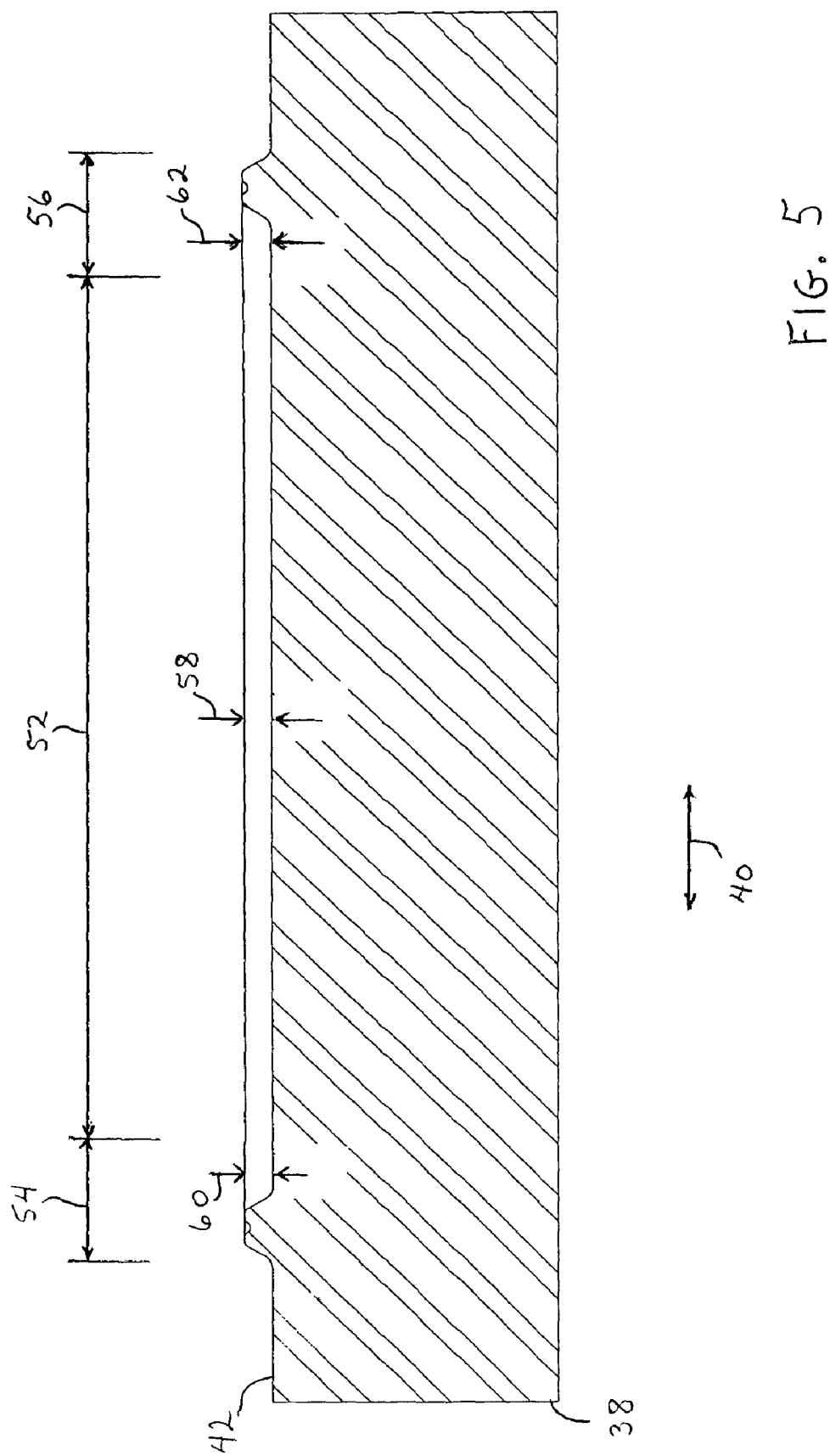
FIG. 5 shows a view of a representative longitudinal cross-section through the view of the flattened embossing member that is representatively shown in FIG. 4.

As representatively shown in FIGS. 4 through 6, the embossing member 44 can include a plurality of two or more channel-elements or embossing-elements. In the representatively shown configuration, for example, the embossing member 44 can include a first, longitudinally-extending, curvilinear or otherwise nonlinear channel embossing-element 72. Additionally, the embossing member can include at least a second, longitudinally-extending, curvilinear or otherwise nonlinear embossing-element 74, which is located proximally adjacent the first embossing-element. The first embossing-element can have a relatively outboard position toward the terminal edges of the target web 26, and the second embossing-element can be arranged with a relatively inboard position toward the center of the target web. The channel embossing-elements may or may not be parallel. Additionally, the traversing occurrences of the embossing-elements may be substantially synchronous or in-phase, or may be nonsynchronous or out-of-phase. The nonsynchronous embossing elements may also have different configurations of their nonlinear patterns, and/or may have different frequencies of occurrence. Where the embossing-elements are nonsynchronous, any or all of the individual embossing-elements may have any or all of the parameters described for the embossing member 44. For example, any or all of the individual embossing-elements may have the undulating shape, lateral traversing distance and/or traversing frequency of occurrence that are described for the embossing member 44. Desirably, each of the individual embossing-elements will operatively cooperate to exhibit the parameters desired for the embossing member 44.

With reference to FIGS. 1A and 1B, there can be a selected separation distance 86 between the proximate, immediately adjacent embossing-elements. As representatively shown, for example, a separation distance between the first and second embossing-elements 72 and 74 can be at least a minimum of about 0.05 cm. The separation distance 86 can alternatively be at least about 0.1 cm, and can optionally be at least about 0.2 cm to provide improved performance. In other aspects, the separation distance can be up to a maximum of about 0.8 cm, or more. The separation distance can alternatively be up to about 0.5 cm, and can optionally be up to about 0.3 cm to provide improved effectiveness.

If the separation distance 86 is outside the desired values, the article formed from the target web 26 can exhibit excessive stiffness, and the definition of the embossment formed in the target web may be less readily perceived. Additionally, the desired liquid wicking along the formed embossment can be degraded. The formed article can also be less able to provide a desired controlled deformation which properly shapes to the contours of the wearer's body. If the separation distance is too large, the liquid may also excessively bridge across the embossment elements formed in the target web 26, resulting in premature leakage.

As representatively shown in FIG. 6, the embossing member 44 can include a plurality of two or more embossing elements. The multi-element embossing member can have an overall, region width 48, as measured between an outboard-edge 90 of a first embossing-element 72 and a correspondingly associated inboard edge 92 of a second embossing-element 74. In particular aspects, the embossing member width 48 can be at least a minimum of about 0.15 cm. The overall embossing member width can alternatively be at least about 0.3 cm, and can optionally be at least about 0.5 cm to provide improved performance. In other aspects, the overall embossing member width can be up to a maximum of about 2.2 cm, or more. The overall embossing member width can alternatively be up to about 1.1 cm, and can optionally be up to about 0.7 cm to provide improved effectiveness.

If the overall width of the embossing member is too low, liquid may excessively bridge over the embossment region 82 formed in the target web 26, and an article 80 formed from the target web may prematurely leak. Additionally, the cover and/or baffle may be excessively susceptible to cut-through during high-speed embossing operations. If the overall width of the embossing member is too large, the article 80 formed from the target web 26 may exhibit excessive stiffness.

With reference to FIG. 6, the first embossing-element 72 can have a first embossing-element width 48a and the second embossing-element 74 can have a second embossing-element width 48b. In a particular feature, the first embossing-element width 48a can be at least a minimum of about 0.05 cm. The first embossing-element width can alternatively be at least about 0.08 cm, and can optionally be at least about 0.1 cm to provide improved performance. In other aspects, the first embossing-element width 48a can be up to a maximum of about 0.7 cm, or more. The first embossing-element width can alternatively be up to about 0.3 cm, and can optionally be up to about 0.2 cm to provide improved effectiveness.

Additionally, the second embossing-element width 48b can be at least a minimum of about 0.05 cm. The second embossing-element width can alternatively be at least about 0.08 cm, and can optionally be at least about 0.1 cm to provide improved performance. In other aspects, the second embossing-element width 48b can be up to a maximum of about 0.7 cm, or more. The second embossing-element width can alternatively be up to about 0.3 cm, and can optionally be up to about 0.2 cm to provide improved effectiveness.

If the embossing-element width 48a and/or 48b is too large, the product formed from the target web 26 can exhibit excessive stiffness. If the embossing-element width 48a and/or 48b is too small, liquid may excessively bridge across the embossing member to cause premature leakage in the product formed from the target web. Additionally, the cover and/or baffle materials in the target web 26 may be excessively susceptible to cut-through during the embossing operation.

Figure 7:
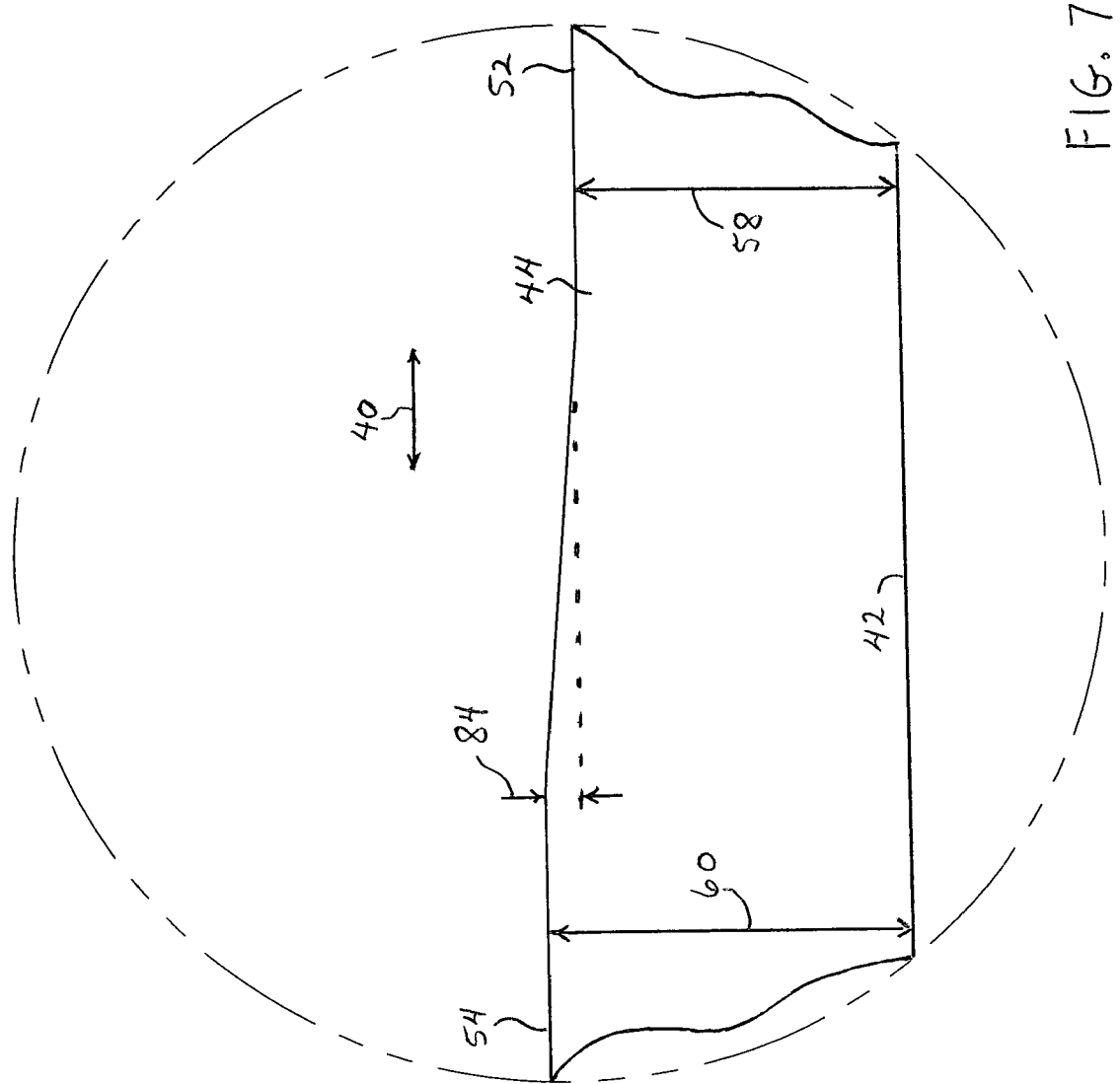
FIG. 7 shows an enlarged view of a stepped region of the embossing member illustrated in FIG. 4.

The rotary embossing device 38 can be configured to include a distinctive stepped configuration, as observed along the circumferential-direction of its outer peripheral surface 42. In a particular aspect, the embossing member 44 can have a stepped configuration. With reference to FIGS. 3, 7 and 7A, the embossing member 44 can be configured to include a first embossing-member segment 52, and at least a second embossing-member segment 54 which is located circumferentially adjacent a first longitudinal end of the first embossing-member segment. The first embossing-member segment 52 can include a first radial height 58 extending radially outward from the outer peripheral surface 42 of the embossing device 38, and the second embossing-member segment 54 can include a second radial height 60 which is greater than the first radial height. The first embossing-member segment 52 and the second embossing-member segment 54 can have a distinctive height difference 84. In a particular aspect, the height difference can be at least a minimum of about 0.025 mm. The height different can alternatively be at least about 0.08 mm, and can alternatively be at least about 0.13 mm to provide improved performance. In another aspect, the height difference can be up to about 0.25 mm, or more. The height difference can alternatively be up to about 0.22 mm, and can optionally be up to about 0.18 mm to provide improved performance. If the height difference is outside the desired values, the target web can experience uneven embossing across its different regions. For example, the target web can contain embossed areas that are undesirable hard/stiff, and/or embossed regions that are poorly formed. Additionally, if the height difference is inadequate, the cover and/or baffle materials in the target web 26 may be excessively susceptible to cut-through during the embossing operation.

In a further feature, the rotary embossing device 38 can be configured to include a third embossing-member segment 56, and the third device segment can include a third radial height 62 which is greater than the first radial height 58. As representatively shown in FIG. 6, the third segment 56 may be located circumferentially adjacent second longitudinal end of the first device segment. The third device segment 56 can include a third radial height which is greater than the first radial height. The first device segment 52 and the third device segment 56 can have a distinctive height difference 84a. In a particular aspect, the height difference can be at least a minimum of about 0.025 mm. The height difference can alternatively be at least about 0.08 mm, and can alternatively be at least about 0.13 mm to provide improved performance. In another aspect, the height difference can be up to about 0.25 mm, or more. The height difference can alternatively be up to about 0.22 mm, and can optionally be up to about 0.18 mm to provide improved performance.

In another aspect of the process and apparatus, the contacting of the target web 26 with the rotary embossing device 38 can be configured to provide a selected embossing force value. The embossing force value can be at least a minimum of about 3×10⁶ Newtons per meter of cross-directional width of the embossing pattern (N/m), e.g. as found in the nip region between the rotary embossing device 38 and the rotary anvil 70. In a particular arrangement, the embossing force can be about 12,000 N (about 2,700 lb$_f$) applied to a 4 mm, total cross-directional length of embossing member contact with the target web that is provided in the embossing nip region. In another aspect, the embossing force value can be up to about 5×10⁷ N/m in the nip region to provide improved performance. In a particular arrangement, the embossing force can be about 2×10⁵ N (about 45,000 lb$_f$) applied to a 4 mm, total cross-directional length of embossing member contact with the target web that occurs in the embossing nip region. With reference to the embossing pattern illustrated in FIG. 2 that is produced with the embossing component illustrated in FIGS. 4 and 6, for example, the total cross-directional length (W$_T$) of the distal outward surface of the embossing member that contacts and embosses the target web in the embossing nip region. The width of the embossing pattern of the embossing member would be determined by the following calculation:

$$W_T = 2*(\text{Element Width } 48a) + 2*(\text{Element Width } 48b)$$

If the embossing force is too low, light embossing or under-embossing can occur when operating at high embossing speeds. If the embossing force is too high and/or the nip gap is too small, the embossed areas may be too stiff and the apparatus and process may experience upsets due to jams within the embossing system.

With reference again to FIG. 1, the apparatus and process can further include an attaching of the composite web 26 to a layer or other web of baffle material 36. In a particular aspect, the attaching of the baffle web 36 can occur after the occurrence of the contacting of the composite web 26 with the rotary embossing device 38.

The baffle layer web 36 may include a layer constructed of any operative material, and may or may not have a selected level of liquid-permeability or liquid-impermeability, as desired. In a particular configuration, the backsheet or baffle layer web 36 may be configured to provide an operatively liquid-impermeable baffle structure. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the baffle layer web 36 can operatively permit a sufficient passage of air and moisture vapor out of the article, particularly out of an absorbent (e.g. storage or absorbent structure 30) while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-li.Jungan-mvu.Kongiu-City, Chungcheong nam-do, Republic of South Korea. The baffle material is a breathable film, which is dimple embossed and contains: 47.78% calcium carbonate, 2.22% TiO$_2$, and 50% polyethylene.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A process for forming an embossed article, comprising moving a target web along an appointed machine-direction at a web speed which is at least about 1.9 m/sec; and operatively contacting said target web with a rotary embossing device to thereby form a nonlinear embossment region in at least a target portion of said target web;

wherein said embossing device includes an outer peripheral surface having a lateral cross-direction and a circumferential-direction, and includes a nonlinear embossing member located on said outer surface;

said embossing member has been configured to include a traversing occurrence of at least 1.5 cycles within a 5 cm length along the circumferential-direction of said embossing device; and said embossing member has been configured to include a lateral traversing distance which is at least a minimum of about 0.5 cm.

2. A process as recited in claim 1, wherein said web speed is up to about 7.5 m/sec.

3. A process as recited in claim 1, wherein said target web has been tensioned to provide a web-strain, and the web strain is up to about 5%.

4. A process as recited in claim 1, wherein said rotary embossing device has been configured to include a stepped configuration, as observed along the circumferential-direction of its outer peripheral surface.

5. A process as recited in claim 4, wherein said rotary embossing device has been configured to include a first device segment, and at least a second device segment which is located circumferentially adjacent the first device segment;

said first device segment has included a first radial height;

said second device segment has included a second radial height which is greater than said first radial height;

said first device segment and said second device segment have a height difference which is at least a minimum of about 0.025 mm.

6. A process as recited in claim 5, wherein said first device segment and said second device segment have a height difference which is up to a maximum of about 0.25 mm.

7. A process as recited in claim 4, wherein said rotary embossing device has been configured to include a third device segment; and said third device segment has included a third radial height which is greater than said first radial height.

8. A process as recited in claim 1, wherein said target web has included a cover layer and at least one absorbent body member; and said absorbent body member has included cellulosic fibers.

9. A process as recited in claim 8, wherein the cellulosic fibers have been provided with a moisture content which is at least about 4 wt %.

10. A process as recited in claim 8, wherein the cellulosic fibers have been treated with a friction-reducing material.

11. A process as recited in claim 8, wherein the cellulosic fibers have been configured to be substantially free of separately provided debonding agents.

12. A process as recited in claim 1, wherein said embossing member has a member height which is at least a minimum of about 2 mm.

13. A process as recited in claim 12, wherein said embossing member has a member height which is up to a maximum of about 13 mm.

14. A process as recited in claim 1, wherein said embossing member has a member width which is at least a minimum of about 0.5 mm.

15. A process as recited in claim 14, wherein said embossing member has a member width which is up to a maximum of about 7 mm.

16. A process as recited in claim 1, wherein said embossing device has been configured to provide a rotary embossing roll.

17. A process as recited in claim 16, wherein said embossing roll has a roll radius which is at least a minimum of about 7.5 cm.

18. A process as recited in claim 16 wherein said embossing roll has a roll radius which is up to a maximum of about 32 cm.

19. A process as recited in claim 1, wherein said embossing device has been positioned cooperatively adjacent an anvil member.

20. A process as recited in claim 1, wherein the contacting of said target web with said rotary embossing device provides an embossing force value which is at least a minimum of about $3\times10^8$ N/m.

21. A process as recited in claim 20, wherein the embossing force value is up to a maximum of about $5\times10^7$ N/m.

22. A process as recited in claim 1, wherein said embossing member has included sidewall regions, and said sidewall regions have included a sidewall angle which is at least a minimum of about 5 degrees.

23. A process as recited in claim 22, wherein said sidewall angle is up to a maximum of about 45 degrees.

24. A process as recited in claim 1, wherein said embossing member has included a first, relatively outboard embossing element, and at least a second embossing element which is located relatively inboard and proximally adjacent the first embossing element.

25. A process as recited in claim 1, further comprising:
attaching said target web to a layer of baffle material, said attaching occurring after the contacting of said target web with said rotary embossing device.

* * * * *